United States Patent
Davalian et al.

(10) Patent No.: US 8,709,473 B1
(45) Date of Patent: Apr. 29, 2014

(54) METHOD OF TARGETING HYDROPHOBIC DRUGS TO VASCULAR LESIONS

(75) Inventors: Dariush Davalian, San Jose, CA (US);
John Stankus, Campbell, CA (US);
Yuet Mei Khong, Singapore (SG); O. Mikael Trollsas, San Jose, CA (US);
Syed F. A. Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 788 days.

(21) Appl. No.: 12/361,470

(22) Filed: Jan. 28, 2009

(51) Int. Cl.
*A61K 9/127* (2006.01)

(52) U.S. Cl.
USPC ........................................................ 424/450

(58) Field of Classification Search
USPC ........................................................ 424/450
See application file for complete search history.

(56) References Cited

U.S. PATENT DOCUMENTS

| | | | | |
|---|---|---|---|---|
| 5,482,719 | A | * | 1/1996 | Guillet et al. ................ 424/486 |
| 2002/0051812 | A1 | * | 5/2002 | DiCosmo et al. ............ 424/450 |
| 2002/0061330 | A1 | * | 5/2002 | Chowdhary et al. ......... 424/450 |
| 2005/0107329 | A1 | * | 5/2005 | Desai et al. .................. 514/53 |
| 2005/0244401 | A1 | * | 11/2005 | Ingenito .................... 424/94.64 |
| 2006/0110425 | A1 | * | 5/2006 | Latrille et al. ............... 424/423 |
| 2007/0231375 | A1 | * | 10/2007 | Tsai et al. .................... 424/450 |
| 2010/0247447 | A1 | * | 9/2010 | Boch et al. .................. 424/9.61 |

FOREIGN PATENT DOCUMENTS

| | | | |
|---|---|---|---|
| WO | 02/03800 | * | 1/2002 |
| WO | WO 02/096366 | | 12/2002 |

OTHER PUBLICATIONS

Derwent-ACC No. 2008-M47686.*
"Photodynamic Therapy for Cancer:Questions and Answers", National Cancer Institute, downloaded from www.cancer.gov/cancertopics/factsheet/Therapy/photodynamic, Jun. 16, 2008, 3 pgs.
"What is Photodynamic Therapy?", downloaded from www.cancer.org/docroot/ETO/content/ETO, Jun. 16, 2008, 1 pg.
Biade et al., "Photosensitization by Photofrin II Delivered to W126VA4 SV40-Transformed Human Fibroblasts by Low Density Lipoproteins: Inhibition of Lipid Synthesis and Fatty Acid Uptake", Photochemistry and Photobiology, vol. 55, No. 1, pp. 55-61 (1992).
Casella et al., "Haem-Protein Interactions. The Binding of Haem Complexes to Serum Albumin", Gazzetta Chimica Italiana 123, pp. 149-154 (1993).
Chowdhary et al., "Drug release characteristics of lipid based benzoporphyrin derivative", J. Pharm. Pharmaceut. Sci. 6, pp. 13-19 (2003).
Dockal et al., The Three Recombinant Domains of Human Serum Albumin, The J. of Biological Chem. vol. 274, No. 41, pp. 29303-29310 (1999).
Gossl et al., "Frontiers in Nephrology: Early Atherosclerosis—A View Beyond the Lumen", J. Am. Soc. Nephrol 18, pp. 2836-2842 (2007).
Hrkal et al., "Haeme Binding to Human Serum Albumin and to the Three Large Cyanogen Bromide Albumin Fragments", J. Biochem. vol. 9, pp. 349-355 (1978).
Kharbanda et al., "The Atherosclerosis Time-Line and the Role of the Endothelium", Curr. Med. Chem.—Immun. Endoc. & Metab. Agents 5, pp. 47-52 (2005).
Korbelik "Cellular Delivery and Retention of Photofrin: III. Role of Plasma Proteins in Photosensitizer Clearance from Cells", Photochemistry and Photobiology, vol. 57, No. 5, pp. 846-850 (1993).
Maiya "Insights into years 10-12 Physics Problems Solving", Journal Resonance vol. 5, No. 6, pp. 15-29 (2000) Abstract.
Monzani et al., "Binding and Relaxometric Properties of Heme Compexes with Cyanogen Bromide Fragments of Human Serum Albumin", Biophysical J. vol. 83, pp. 2248-2258 (2002).
Monzani et al., "Enzymatic properties of human hemalbumin", Biochimica et Biophysics ACTA 1547, pp. 302-312 (2001).
Neri et al., "Determination of the photodynamic activity of porphyrins: Potential photosensitizers for treatment of age-related macular degeneration", Materials Science, vol. 20, No. 2, pp. 97-103 (2002).
Ohnishi et al., "A comparative Pharmacokinetic Study of Recombinant Human Serum Albumin with Plasma-derived Human Serum Albumin in Patients with Liver Cirrhosis", J. Clin. Pharmacol 48, pp. 203-208 (2008).
Peters "All about Albumin", Academic Press Publ. (1996) 2 pgs. Abstract.
Star "In vivo action spectra, absorption and fluorescence excitation spectra of photosensitizers for photodynamic therapy", J. of Photochem. and Photobiology vol. 28, No. 1, pp. 101-102 (1995) Abstract.
Waksman et al., "Intracoronary photodynamic therapy reduces neointimal growth without suppressing re-endothelialisation in a porcine model", Heart 92, pp. 1138-1144 (2006).
Chowdhary et al., "Correlation of photosensitizer delivery to lipoproteins and efficacy in tumor and arthritis mouse models; comparison of lipid-based and Pluronic® P123 formulations", J. Pharm. Pharmaceut. Sci. 6(2), pp. 198-204 (2003).
Fogelman et al., Lipoproteins and Atherosclerosis—The Role of HDL Cholesterol, Lp (a) and LDL Particle Size, downloaded from: http://www.medscape.com/viewarticle/439375, Jan. 26, 2009, 4 pgs.
Lee et al., "Prospects for atherosclerosis regression through increase in high-density lipoprotein and other emerging therapeutic targets", in: www.heartjnl.com, pp. 559-564 (2006).
Rockson et al., "Photoangioplasty for Human Peripheral Atherosclerosis: Results of a Phase I Trial of Photodynamic Therapy with Motexafin Lutetium (Antrin)", Circulation 102, pp. 2322-2324 (2000).
Rockson et al., "Photoangioplasty: An Emergin Clinical Cardiovascular Role for Photodynamic Therapy", Circulation 102, pp. 591-596 (2000).

* cited by examiner

*Primary Examiner* — Gollamudi Kishore
(74) *Attorney, Agent, or Firm* — Squire Sanders (US) LLP (57) ABSTRACT

This invention relates to the targeted delivery of hydrophobic drugs or combinations of hydrophobic drugs with photodynamic therapy agents to vascular lesions by complexation of the drugs to blood serum lipoproteins, which have an affinity for and accumulate in such vascular lesions.

15 Claims, 1 Drawing Sheet

METHOD OF TARGETING HYDROPHOBIC DRUGS TO VASCULAR LESIONS

FIELD

The current invention is related to the field of targeted drug delivery.

BACKGROUND

Lesions associated with atherosclerosis and similar diseases of the vasculature in general have been found to comprise cholesterol, cholesterol ester, phospholipid and triglyceride in one or more lipid phases. Katz, S, and Small, Daniel, J. Biol. Chem., 255(20):9753-59 (1980). The lipophilic nature of the lesions renders them naturally compatible with blood serum lipoproteins such that serum lipoproteins tend to shuttle in and out of the lesions. Exacerbating this effect is the fact that the cells comprising the surface of such lesions generally exhibit the phenomenon known as enhanced permeability and retention (EPR).

The EPR effect, which was first described with regard to the preferential permeation into, and retention by, tumor tissues of serum proteins but which has since been found to extend to many types of diseased tissues including vascular lesions, is the result of defective tissue architecture, changes in permeation mediators and impaired lymphatic drainage. That is, the vascular endothelium of tumors and vascular lesions tends to have relatively large gaps in the endothelial cell-cell junctions compared to normal tissue. This permits larger molecular species to permeate the tissue than is the case for healthy tissue. The altered permeation mediators and impaired lymphatic drainage mechanism assure that the molecules that have penetrated the lesion stay there. The EPR effect has been used in practice to selectively introduce and retain chemotherapeutics in tumors by tethering small molecule drugs to polymers or nanoparticles that are too large to permeate normal tissue but that readily infiltrate tumor tissue.

What would be valuable would be a method of using the affinity of vascular lesions for serum lipoproteins together with the EPR effect to direct, i.e., target, therapeutic agents to the damaged tissue. This invention provides such a method.

SUMMARY

Thus, in one aspect, the current invention relates to a method of targeting drug delivery to a vascular lesion, comprising:
providing a core-shell carrier comprising a lipophilic shell layer that is unstable to a plasma protein;
providing a non-photodynamic hydrophobic drug loaded into the core-shell carrier, and administering the drug-loaded core-shell carrier into the bloodstream of a patient in need thereof; wherein, when the core-shell carrier contacts a plasma protein in the patient's bloodstream, the core-shell carrier is disrupted, releasing the non-photodynamic hydrophobic drug which then forms a complex with a plasma protein that may be the same as or different than the plasma protein that caused the disruption of the core-shell carrier.

In an aspect of this invention, the core-shell carrier is selected from the group consisting of a plasma protein unstable micelle, a plasma protein unstable liposome and a plasma protein unstable polymersome.

In an aspect of this invention, the core-shell carrier comprises a plasma protein unstable liposome.

In an aspect of this invention, the non-photodynamic drug is loaded into a lipid bilayer of the plasma protein unstable liposome.

In an aspect of this invention, the plasma protein unstable liposome comprises soy phosphatidylglycerol, hydrogenated soy phosphatidylglycerol, distearoyl phosphatidylglycerol, soy phosphatidylcholine, hydrogenated soy phosphatidylcholine or any combination thereof.

In an aspect of this invention, the non-photodynamic drug is complexed to a photodynamic therapy agent.

In an aspect of this invention, the photodynamic therapy agent comprises a porphyrin.

In an aspect of this invention, the drug-porphyrin complex comprises a biocompatible, biodegradable linker joining the drug to the porphyrin.

In an aspect of this invention, the porphyrin comprises a deuteroporphyrin IX diester.

In an aspect of this invention, the diester is a dimethyl ester.

In an aspect of this invention, the vascular lesion comprises an atherosclerotic plaque, a restenotic lesion, a vulnerable plaque or a peripheral arterial lesion.

In an aspect of this invention, the plasma proteins comprise low density lipoprotein, high density lipoprotein, human serum albumin or any combination thereof.

In an aspect of this invention, the non-photodynamic hydrophobic drug is selected from the group consisting of rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, zotarolimus, everolimus, biolimus, temsirolimus, AP23573, deforolimus, novolimus, myolimus and derivatives, analogs, prodrugs, co-drugs and combinations of any of these.

In an aspect of this invention, the non-photodynamic hydrophobic drug is selected from the group consisting of everolimus and zotarolimus.

In an aspect of this invention, the drug-laden plasma protein unstable core-shell carrier is administered systemically.

In an aspect of this invention, the drug-laden plasma protein unstable core-shell carrier is administered locally.

In an aspect of this invention, local administration comprises us of an implantable medical device.

In an aspect of this invention, the implantable medical device is a stent.

DETAILED DESCRIPTION

Brief Description of the Tables

Table 1 shows the fluorescence units on interaction between 5:50 gallium chloride deuteroporphyrin IX dimethyl ester:lipid (3:1 Soy-PC:DSPG) liposome, empty liposome (3:1 Soy-PC:DSPG) and PBS.

Table 2 shows fluorescence units on interaction between 1:20 gallium chloride deuteroporphyrin IX dimethyl ester:lipid (2:1 Soy-PC:DSPG) liposome, human serum albumin (HSA) and PBS.

Table 3 shows fluorescence units on interaction between 1:20 gallium chloride deuteroporphyrin IX dimethyl ester:lipid (3:1 Soy-PC:DSPG) liposome, human serum albumin (HSA) and PBS.

Table 4 shows fluorescence units on interaction between 1:20 gallium chloride deuteroporphyrin IX dimethyl ester:lipid (2:1 Soy-PC:DSPG) liposome, HDL or LDL, and PBS.

Table 5 shows fluorescence units on interaction between 1:20 gallium chloride deuteroporphyrin IX dimethyl ester:lipid (3:1 Soy-PC:DSPG) liposome, HDL or LDL, and PBS.

DISCUSSION

It is understood that throughout this application including the claims use of the singular includes the plural and vice versa unless expressly stated otherwise. That is, "a" and "the" are to be construed as referring to one or more of whatever the word modifies. Non-limiting examples include: "a drug," which is understood to include one drugs, two drugs or, under the right circumstances, as determined by those skilled in the treatment of diseased tissues, even more drugs unless it is expressly stated or is unambiguously obvious from the context that such is not intended. Likewise, "a core-shell carrier" refers to a single such entity or a plurality of such entitles unless, again, it is expressly stated or absolutely obvious from the context that such is not intended.

The use of words or approximation herein, such as "about" or "approximately" when used to describe numerical values or ranges likewise are understood to mean that those skilled in the art would readily consider a value different from the exact number or outside the actual range to be close enough to be within the aegis of that number or range. At the very least, "about" or approximately is understood to mean±15% of a given numerical value or range starting and ending point.

As used herein, "targeting drug delivery" refers to the process by which a drug is preferentially directed to diseased tissue to the minimization, preferably the exclusion, of any delivery to healthy tissue. Numerous means of achieving such are known to those skilled in the art such as including the drug in a carrier that has surface modifications that are known to interact specifically with an entity that exists only at the diseased site and using magnetized particles containing a drug and attracting the particles to the diseased tissue by providing a magnetic field specifically at the site. For the purposes of this invention "targeted drug delivery" refers to the use of the natural affinity of serum lipoproteins for lipid-containing vascular lesions together with the EPR effect at the lesion's surface to preferentially accumulate one or more therapeutic agents within the lesion.

As used herein, a "vascular disease" refers to a disease of the blood vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" or an "atherosclerotic lesion" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition.

The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery or loss of organ function if the artery is peripheral.

"Restenosis" or a "restenotic lesion" refers to the re-narrowing or blockage of an artery at or near where angioplasty or other surgical procedure was previously performed to remove a stenosis. It is usually due to smooth muscle cell proliferation at times accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to neointimal hyperplasia and vasospasm, with smaller rates of dissection and thrombosis or blood-clotting at the site of the procedure. Stent placement essentially eliminates vasospasm and dissections. However, the stented sites are still susceptible to restenosis due to neointimal hyperplasia and abnormal tissue growth at the site of implantation. While the use of IIb-IIIa anti-platelet drugs such as abciximab and epifabatide, which are anti-thrombotic, reduced the occurrence of post-procedure clotting with stents (although stent placement itself can initiate thrombosis). Restenosis tends also to occur at 3 to 6 months after stent placement, but it is not reduced by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time and it is to improved drug-delivery of DESs that this invention is at least in part directed.

"Vulnerable plaque" refers to an atherosclerotic plaque that has the potential of causing a thrombus and is usually characterized by a very thin wall separating a lipid filled, necrotic core from the lumen of an artery. The thinness of the wall renders the plaque susceptible to rupture. When the plaque ruptures, the inner core of lipid-rich plaque is exposed to blood where it has the potential of causing a fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect the presence of vulnerable plaque in the arterial wall. After death, an autopsy can reveal the ruptured plaque in the arterial wall. However, the pre-rupture narrowing of these plaques cannot typically be seen with commonly available medical imaging. Thus, for the purposes of this invention, it may be beneficial to treat a locale of interest where a vulnerable plaque is suspected to be present based on the symptomology at the locale even though the plaque has not been expressly observed. It is expected that serum lipoproteins such as HDL, LDL and HSA will find their way to a vulnerable plaque in the same manner, discussed below, that they are capable of targeting other types of vascular lesions.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage derived enzymatic degradation can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

Peripheral vascular diseases are generally caused by structural changes in blood vessels caused by such conditions as inflammation, hyperlipidemia, diabetes, and tissue damage. A subset of peripheral vascular disease is peripheral artery disease (PAD) or equivalently herein a peripheral arterial lesion. PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

As used herein, the terms "blood serum protein," "plasma protein," "blood serum lipoprotein," "serum protein," "plasma serum protein," "blood plasma lipoprotein" and any other combination of the individual words all refer to the same entities: HDL, LDL and HSA.

As use herein, a "core-shell carrier" refers to a particle comprised of a hollow inner portion, i.e., the core, which is completely enclosed by a relatively thin layer of material, the shell. The shell may be a single layer of material of it may comprise a multi-lamellar structure that can be compared to the layers of an onion. The single layer or one or more of the layers of a multi-lamellar structure may further comprise lipid bilayers having a lipophilic interior and hydrophilic exterior. Examples of "core-shell carriers" include micelles, worm micelles, liposomes and polymersomes.

A micelle refers to a spherical colloidal core-shell structure spontaneously formed by many amphiphilic molecules in an aqueous medium when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants."

Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Therapeutic agents suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the therapeutic agent. In addition because of their nanoscale size, generally from about 5 nm to about 50 nm, micelles have been shown to exhibit spontaneous accumulation in pathological areas with leaky vasculature and impaired lymphatic drainage, i.e., the EPR effect.

Micelles formed from relatively low molecular weight surfactants is that their CMC is usually quite high so that the formed micelles dissociate rather rapidly upon dilution, i.e., the molecules head for open places at the surface of the water with the resulting precipitation of the therapeutic agent. Fortunately, this short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMCs as low as $10^{-6}$ M (molar). Thus, they tend to be stable, at least in the absence of plasma proteins, while at the same time being able to exhibit the beneficial characteristics of surfactant micelles. Any micelle-forming polymer presently known in the art or as such may become known in the future may be used in the method of this invention. Examples of micelle-forming polymers are, without limitation, methoxy poly(ethylene glycol)-b-poly(ε-caprolactone), conjugates of poly (ethylene glycol) with phosphatidylethanolamine, poly (ethylene glycol)-b-polyesters, poly(ethylene glycol)-b-poly (L-aminoacids), poly(N-vinylpyrrolidone)-bl-poly (orthoesters), poly(N-vinylpyrrolidone)-b-polyanhydrides and poly(N-vinylpyrrolidone)-b-poly(alkyl acrylates).

In addition to the classical spherical micelles described above, the methods of this invention may use constructs known as synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being as stable as spherical polymeric micelles but also of being flexible. Polyethylene oxide has been used extensively to create worm micelles with a number of hydrophobic polymers such as, without limitation, poly(lactic acid), poly (ε-caprolactone), poly(ethylethylene) and polybutadiene. A representative description of worm micelle formation, characterization and drug loading can be found in Kim, Y., et al., *Nanotechnoloqv,* 2005, 16:S484-S491. The techniques described there as well as any other that is currently known or may become known in the future may be used in method of this invention.

As used herein, a "liposome" refers to a core-shell structure in which the shell comprises phospholipids or sphigolipids that surround a usually liquid, and in most cases aqueous, core.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)] sodium salt, 1,2-dimyristoyl-sn-glycero-3-[phospho-L-serine] sodium salt, 1,2-dioleoyl-sn-glycero-3-phosphoethanolamine-N-glutaryl sodium salt and 1,1',2,2'-tetramyristoyl cardiolipin ammonium salt.

While liposomes are known to be relatively unstable in the presence of blood serum components, in particular serum proteins such as low density lipoproteins (LDLs), high density lipoproteins (HDLs) and human serum albumin (HAS), for the purposes of this invention liposomes formed of especially susceptible phosphlipids are presently preferred and even more preferred at present are combinations of these phospholipids that create irregular structure and therefore instability in the phospholipid bilayer that forms the shell of the liposome. Such phospholipids include, without limitation, soy phosphatidylglycerol, hydrogenated soy phosphatidylglycerol, distearoyl phosphatidylglycerol, soy phosphatidylcholine and hydrogenated soy phosphatidylcholine and, as noted above, combinations thereof. At present, a preferred combination is soy PC with DSPG at a ratio of about 2:1 to about 3:1.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

The diblock copolymers discussed above with regard to micelle formation can be further modified to form bilayer structures similar to liposomes. The structures are referred to as polymerosomes. Depending on the length and chemical nature of the polymers in the diblock copolymer, polymerosomes can be more or less robust that liposomes. In addition, the ability to control completely the chemical nature of each block of the diblock copolymer permits tuning of the polymerosome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers. Thus, the desired sensitivity to plasma proteins can be tailored to the desired level for a particular use.

Polymerosomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. Polymerosomes can also be prepared by dissolving the diblock copolymer in a solvent and then adding a poor solvent for one of the blocks, which will result in the spontaneous formation of polymerosomes.

As with liposomes, polymerosomes can be used to encapsulate bioactive agents by including the bioactive agent in the water used to rehydrate the copolymer film. Polymerosomes can also be force-loaded by osmotically driving the therapeutic agent into the core of the vesicle. Similarly to liposomes, the loading efficiency of polymerosomes is generally low. Recently, however, a technique has been reported that provides polymerosomes of relative monodispersivity and high loading efficiency; generation of polymerosomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymerosomes on the concentric interfaces of the double emulsion. The actual polymerosomes are formed by completely evaporating the organic solvent from the shell. By this procedure the size of the polymerosomes can be finely controlled and, in addition, the ability to maintain complete separation of the internal fluids from the external fluid throughout the process allows extremely efficient encapsulation. This technique along with any other technique known in the art or as may become known in the future can be used to prepare vesicles of this invention.

As used herein, the terms "drug," "bioactive agent" and "therapeutic agent" are used synonymously and interchangeably to refer to any substance that, when administered in a therapeutically effective amount to a patient suffering from a disease, has a therapeutic beneficial effect on the health and well-being of the patient. A therapeutic beneficial effect on the health and well-being of a patient includes, but is not limited to: (1) curing the disease; (2) slowing the progress of the disease; (3) causing the disease to retrogress; or (4) alleviating one or more symptoms of the disease.

As used herein, a drug also includes any substance that has a prophylactic beneficial effect on the health and well-being of the patient, when administered to a patient known or suspected of being particularly susceptible to a disease. A prophylactic beneficial effect includes, but is not limited to: (1) preventing or delaying on-set of a disease; (2) maintaining a disease at a retrogressed level once such level has been achieved by a therapeutically effective amount of a drug, which may be the same as or different from the drug used in a prophylactically effective amount; or (3) preventing or delaying recurrence of a disease after a course of treatment with a therapeutically effective amount of a drug, which may be the same as or different from the drug used in a prophylactically effective amount.

As used herein, a "non-photodynamic hydrophobic drug" simply refers to a hydrophobic therapeutic agent having a mode of action of which does not entail light activation with the concomitant formation of extremely reactive oxygen species that then intercept and cause the death of cellular entities.

Conversely, a "photodynamic therapy agent" refers to a drug, the mode of action of which is exactly that mentioned above: light activation followed by formation of reactive oxygen species that then interact with and kill nearby cellular structures. Examples of photodynamic therapy agents include porphyrins, porphyrin precursors, texaphyrin, benzochlorin and chlorophyll. A presently preferred PDT agent is deuteroporphyrin IX, in particular deuteroporphyrin IX dimethyl ester.

As used herein, "administering" refers to the act of introducing a therapeutic agent into the body of a patient. For the purposes of this invention, administration can be carried out systemically or locally.

Systemic delivery involves the administration of a drug at a discrete location followed by the dispersal of the drug throughout the patient's body including, of course, to the target treatment site. In order to achieve a therapeutically effective amount of the drug at the afflicted site, it is usually necessary to administer an initial dose substantially greater than the therapeutically effective amount to account for the dilution the drug undergoes as it travels through the body. Systemic delivery is carried out primarily in two ways: introduction of the drug into the digestive tract (enteral administration) or into the vascular system (parenteral administration), either directly such as injection into a vein or an artery or indirectly such as injection into a muscle or into the bone marrow. Delivery by each of these routes is strongly influenced by the so-called ADMET factors: absorption, distribution, metabolism, excretion and toxicity. For enteric administration, such factors as a compound's solubility, its stability in the acidic environs of the stomach and its ability to permeate the intestinal wall all affect the extent to which the drug is absorbed and therefore its bioavailability. For parenteral delivery factors such as enzymatic degradation, the lipophilic/hydrophilic partitioning coefficient, protein binding, etc. will affect the bioavailability of an agent.

Local delivery comprises administration of the drug directly at the target site. The ADMET factors tend to be less important than with systemic administration since the drug is being administered essentially directly to the treatment site. Thus, the initial dose can be at or very close to the therapeutically effective amount. With time, some of the locally delivered therapeutic agent may diffuse over a wider region but such is not the intent of localized delivery and the concentration of the diffused agent will ordinarily be sub-therapeutic, i.e., too low to have a therapeutic effect. Since localized delivery targets only the desired treatment site, it is possible that some of the causal factors of the disease that have spread to as yet non-afflicted regions of the organ at the periphery of the afflicted region may not undergo sufficient treatment, resulting in reoccurrence of the disease. In addition, local delivery tends to be more invasive than systemic delivery.

By "plasma protein unstable" is simply meant that when a core-shell carrier of this invention contacts a serum lipoprotein, in particular at present, human serum albumin (HSA), low density lipoprotein ((LDL) and/or high density lipoprotein (HDL), the shell of the carrier is breached releasing therapeutic agents contained within the core of the particle or, in some instances, agents contained with the lipophilic interior of a lipid bilayer.

As used herein, when it is stated that a drug is "complexed" with another entity, the term refers to the physical bonding of the drug to the structure such that the combined species acts as one unit with regard to transport through a biological system such as the blood stream, the extracellular matrix of a tissue or the surface layer of a cell. Physical bonding includes, without limitation, hydrogen bonding, ionic interactions, dipole-dipole interactions, van der Waals forces, hydrophobic interactions and the like.

While for some time considered to be simply a lipid storage disease, recent studies have demonstrated that atherosclerosis actually involves an on-going inflammatory response. In fact inflammation has been established as having a fundamental role in mediating virtually all stages of the disease from initiation through progression and ultimately to the thrombotic complications associated with atherosclerosis. For example, blood leukocytes, mediators of host defenses and inflammation, have been shown to localize in the earliest lesions of atherosclerosis. The normal endothelium does not in general support binding of white blood cells but in the early stages of atherosclerosis patches of arterial endothelial cells have been observed to express on their surface selective adhesion molecules that bind to various classes of leukocytes. In particular expression of vascular cell adhesions molecule-1 (VCAM-1) has been observed on endothelial cells overlying nascent atheroma. VCAM-1 binds both monocytes (macrophage precursors) and T lympocytes, both of which are involved in inflammatory responses. Libby, et al., *Circulation*, 2002, 105:1135. Thus, a presently preferred family of therapeutic agents for use in conjunction with a PDT agent in the method of this invention are the anti-inflammatory agents. Anti-inflammatory agents useful herein include, but are not limited to, statins, corticosteroids, and antioxidants.

Statins are of particular interest because of their potential dual role in the treatment of atherosclerosis. That is, the primary function for which they are generally prescribed is to lower the production of cholesterol by the liver by blocking the enzyme 3-hydroxy-3-methylglutaryl-coenzyme A reductase (HMG-CoA reductase)A. As noted above, cholesterol plays a key role in the formation of atherosclerotic lesions so a reduction in its production should be a major benefit to patients susceptible to or afflicted with atherosclerosis. The results of many clinical studies, however, have shown the improvement in cardiovascular risk reduction obtained from the administration of statins to be superior to the estimations calculated from the effect on LDL cholesterol lowering. Recent studies have shown that statins have an inhibitory effect on the monocyte-endothelial interaction discussed above suggesting an anti-inflammatory effect as well as a cholesterol lowering effect. Useful statins include, but are not limited to, atorvastatin (Lipitor®), lovastatin (Mevacor®), simvastatin (Zocor®), fluvastatin (Lescol®) and pravastatin (Pravachol®).

Another class of drugs for use in the method of this invention is the corticosteroids. Corticosteroids include cortisol, an adrenal hormone found naturally in the body, as well as synthetic drugs. They all are potent anti-inflammatory compounds with the synthetic corticosteroids exerting the strongest effects. Corticosteroids potentially useful in the method of this invention include, but are not limited to, alclometasaone, amcinonide, betamethasone, clobestasole, clocortalone, desonide, desoxymetasone, diflorasone, flucinolone, fluocinonide, flurandrenolide, fluticasone, halcinonide, halobetasol, hydrocortisone, methylprednisolone, mometasoneprednicarbate, triamcinolone.

Additional therapeutic agents that are presently preferred for use in the method of this invention are rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, zotarolimus, everolimus, biolimus, temsirolimus, AP23573, deforolimus, novolimus, myolimus, paclitaxel and 17-allylamino-17-demethoxygelanamycin (17-AAG) and derivatives, analogs, prodrugs, co-drugs and combinations of any of these.

Of course, a host of other therapeutic agents may be incorporated into the method of this invention as their use is developed, expanded and found to be applicable to the diseases and disorders indicated herein.

Bioactive agents useful with the present invention include, without limitation, an anti-stenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-enzymatic agent, an angiogenic agent, a cyto-protective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, everolimus, biolimus, perfenidone and derivatives, analogs, prodrugs, co-drugs and combinations of any of the foregoing.

Examples of anti-inflammatory agents include, without limitation, both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, diflu-
prednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs, co-drugs and combinations of any of the foregoing.

Examples of antineoplastics and antimitotics include, without limitation, paclitaxel, docetaxel, methotrexate, azathioprine, vincristine, vinblastine, fluorouracil, doxorubicin hydrochloride, and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO) and derivatives, analogs, prodrugs, codrugs and combinations thereof.

Examples of cytostatic agents include, without limitation, angiopeptin, angiotensin converting enzyme inhibitors such as captopril, cilazapril or lisinopril, calcium channel blockers such as nifedipine; colchicine, fibroblast growth factor (FGF) antagonists, fish oil (ω-3-fatty acid), histamine antagonists, lovastatin, monoclonal antibodies such as, without limitation, those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine (a PDGF antagonist) and nitric oxide.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, PFO closure devices, arterial closure devices, artificial heart valves and cerebrospinal fluid shunts.

An implantable medical device specifically designed and intended solely for the localized delivery of a therapeutic agent is within the scope of this invention.

At present, a preferred implantable medical device comprises a stent.

A stent refers generally to any device used to hold tissue in place in a patient's body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and vulnerable plaque. For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. Indeed, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. Due to the expansion of the stent, a stent coating must be flexible and capable of elongation.

Exemplary stent materials include, but are not limited to, stainless steel, nitinol, tantalum, tantalum alloy, titanium, titanium alloy, cobalt chromium, alloy x, niobium, niobium alloy, zirconium and zirconium alloy.

A "patient" refers to any species that might benefit from treatment using the method herein but at present is preferably a mammal and most preferably a human being.

As used herein, "treating" refers to the administration of a therapeutically effective amount of a bioactive agent to a patient known or suspected to be suffering from a vascular disease.

A "therapeutically effective amount" refers to that amount of a therapeutic agent that will have a beneficial effect, which may be curative or palliative, on the health and well-being of the patient so afflicted.

As used herein, a "linker" refers to a chemical moiety that has at least two functional groups, one of which permits it to chemically bind to a porphyrin molecule and the other of which permits it to chemically bind to a desired drug molecule thus linking the drug to the porphyrin. A non-limiting example of such a porphyrin having a potential linking functional group is deuteroporphyrin IX which has two carboxylic acid groups such that a linker having a hydroxyl group could be used to form an ester bond, an amine-containing linker could be used to from an amide bond and the like. Appropriate groups on drugs and corresponding groups on the linker should be apparent to those skilled in the art based on the disclosure herein.

As used herein, "biocompatible" refers to a property of a material characterized by it, or its physiological degradation products, being not, or at least minimally, toxic to living tissue; not, or at least minimally and reparably, otherwise injurious living tissue; and/or not, or at least minimally and controllably, causative of an immunological reaction in living tissue. With regard to salts, both the cation and anion must be biocompatible.

As used herein, a "biodegradable linker" refers to a linker that comprises at least one structural feature, usually a functional group such as, without limitation, an ester, an aldol, a ketal, an imine, an anhydride or a carbonate that is susceptible to cleavage under physiological conditions such as pH, temperature, enzymatic activity and the like.

Porphyrins are known to complex readily and strongly with serum proteins such as HSA, LDL and HDL. While complexation with HSA is less than that with LDL and HDL, HSA exists in blood at a substantially higher concentration that LDL and HDL which makes up for the deficiency.

Since, as mentioned above, it is known that the serum lipoproteins have a natural affinity for the lipophilic constituents of vascular lesions and porphyrins have an affinity for serum lipoproteins, it is an aspect of this invention that PDT porphyrins be administered directly into the blood stream of a patient in need of treatment upon which the porphyrin will complex with the lipoproteins in the blood serum and then be transported systemically throughout the patient's body but, due to the above affinity for vascular lesions and augmented by the EPR effect, the porphyrin-LDL, porphyrin-HDL or porphyrin HSA complex will tend to accumulate at the lesion, i.e., the targeted delivery of this invention will be accomplished. Once within the lesion, the porphyrin can release from the complex at which time the hydrophobic nature of the porphyrin itself will allow the drug to distribute into the lipid rich tissue.

While a PDT drug, in particular porphyrins, can be administered directly, it would be beneficial to administer them within a carrier, in particular a core-shell carrier of this invention. Not only would the core-shell carrier protect the drug and thereby enhance its potency, the core-shell carrier, having a relatively hydrophilic exterior, would be more compatible with the essentially aqueous blood stream until a serum lipoprotein is encountered. In order for an encapsulated PDT drug to bind to a serum lipoprotein, however, it would be necessary for the core-shell carrier, be it a micelle, a liposome or a polymerosome, to break down and release the PDT drug. It has been found that certain liposomal structures have such properties, in particular, but without limitation, liposomes whose shell is comprised of soy PC, soy PG, HSPG, HSPC and DSPG, preferably at present soy PC and DSPG.

The above properties of porphyrin PDTs can be used to deliver in a targeted manner other drugs to lesions simply by linking the drug to the porphyrin and allowing the above chain of events to occur.

Of course, if desired, other drugs may take advantage of the same phenomenon as porphyrins. That is, any lipophilic drug may complex with serum lipoproteins and be transported to a vascular lesion in the same manner as a PDT porphyrin. Many of the non-PDT drugs disclosed above are in fact lipophilic and would be expected to respond in the same manner as a porphyrin PDT. Based on the disclosure herein, those skilled in the art will be readily able to determine which of the listed drugs are sufficiently lipophilic to complex with serum lipoproteins and thereupon be transported with the lipoprotein to a vascular lesions site. As with the PDT porphyrins, it is presently preferred to encapsulate the non-PDT lipophilic drug in a core-shell carrier for initial delivery into a patient with the core-shell carrier disintegrating in the presence of the lipoprotein, thereby releasing the drug which will complex with the same lipoprotein that caused disruption of the core-shell carrier or with another lipoprotein in the vicinity.

EXAMPLES

To demonstrate that the liposomes of the current invention are indeed labile under physiological conditions, that is, when contacted with serum proteins, and that a hydrophilic drug loaded into the liposomes would have an affinity for another lipid entity, the following experiments were conducted using as a non-limiting test drug complex gallium chloride-deuteroporphryin IX dimethyl ester and, as the core shell carrier, a liposome having as it shell a combination of PC and DSPG at different ratios.

Example 1

Example 1 demonstrates the lability of drug-loaded liposomes in the presence of another lipophilic entity, here empty liposomes of the same composition as the drug-loaded liposomes. A control using drug-loaded liposomes in PBS was also used.

Gallium Chloride deuterophorphorin IX dimethyl ester (GC-DPDE) was prepared and diluted to give 0.1 to 0.2 Absorbance Units (AUs) under UV-VIS spectroscopy. The GC-DPDE was loaded by conventional techniques into soy PC-DSPG, 3:1 ratio, liposomes in which the GC-DPDE to lipid ratio was 5:20, the ratio being selected so as to quench initial fluorescence. The resultant liposomes had an average diameter of about 76 nanometers (nm). Liposomes containing no GC-DPDE were also prepared at the same soy PC-DSPG ratio. The GC-DPDE-laden liposomes were then contacted with empty liposomes and with standard saline solution (PBS) by extracting 0.2 ml of drug-loaded liposome and replacing with 0.2 ml of either empty liposome or PBS and screening using a microplate reader to determine the amount of drug, if any, that was released from the heavily loaded liposome by the empty liposome or into the PBS. The results of the experiments are shown in Table 1.

TABLE 1

Fluorescence units upon interaction between 5:20 GALLIUM CHLORIDE DEUTEROPORPHYRIN-IX DIMETHYL ESTER:Lipid (3:1 Soy-PC:DSPG) liposome, empty liposome (3:1 Soy-PC:DSPG) and PBS

| Amount of empty liposome or PBS transfer (ml) | 5:20 GALLIUM CHLORIDE DEUTEROPORPHYRIN-IX DIMETHYL ESTER:Lipid PORPHRIN (3:1 Soy-PC:SDPG) Liposome Solution (4ml):( | | | | | | (a)(iii) PBS Solution (4 ml), Fluorescence units upon empty liposome transfer |
|---|---|---|---|---|---|---|---|
| | (a)(i) Fluorescence Units upon empty liposome (3:1 Soy-PC:DSPG) transfer | | | (a)(ii) Fluorescence units upon PBS Transfer | | | |
| | Average | 1st set | 2nd set | Average | 1st set | 2nd set | |
| 0.0 | 453.38 | 453.58 | Not recorded | 363.72 | 359.67 | 367.76 | Not recorded |
| 0.2 | 309.02 | 309.94 | 308.10 | 319.10 | 319.71 | 318.48 | 2.07 |
| 0.4 | 380.04 | 379.01 | 381.07 | 270.71 | 271.20 | 270.21 | 4.86 |
| 0.6 | 444.16 | 442.86 | 445.46 | 230.63 | 230.12 | 231.14 | 6.19 |
| 0.8 | 484.88 | 485.90 | 483.86 | 203.30 | 204.36 | 202.24 | 7.19 |
| 1.0 | 504.79 | 504.33 | 505.25 | 177.62 | 177.16 | 178.07 | 8.49 |
| 1.2 | 517.59 | 518.25 | 516.93 | 152.15 | 153.17 | 151.13 | 8.97 |
| 1.4 | 527.94 | 530.65 | 525.22 | 128.20 | 129.77 | 126.63 | 8.62 |

The microplate reader shows that the initial fluorescence quenching due to the heavily-loaded drug-liposome disappeared and fluorescence increased as the amount of empty liposome was increased in 0.2 ml increments. This suggests that some drug from the heavily-loaded liposome distributed to the empty liposomes leading to overall drug dilution in the liposomes and a concomitant increase in intrinsic fluorescence.

Transferring PBS into the heavily-loaded drug-liposome, on the other hand, resulted in no effect on the initial fluorescence quenching.

Example 2

Example 2 demonstrates the lability of liposomes of this invention in the presence of HSA with PBS again used as a control comparison. Soy PC:DSPG shell liposomes at ratio of 2:1 and 3:1 were again used and the GC-DPDE was again diluted until UVNIS spectroscopy afforded a 0.1-0.2 AU reading. The drug:lipid ratio was set at 1:20. The average liposome size was 83.3 nm. The GC-DPDE-laden liposomes were then contacted with HSA (Sigma-Aldrich A8763-5G, dissolved in PBS to a concentration of 10 mg/ml) and with standard saline solution (PBS) by extracting 0.2 ml of drug-loaded liposome and replacing with 0.2/0.4 ml of either HSA or PBS and screening using a microplate reader to determine the amount of drug, if any, that was released from the heavily loaded liposome by the HSA or into the PBS The results are shown in Tables 2 and 3.

TABLE 2

Fluorescence units upon interaction between
1:20 GALLIUM CHLORIDE DEUTEROPORPHYRIN-IX DIMETHYL ESTER:Lipid
(2:1 Soy-PC:DSPG) liposome, Human Serum Albumin and PBS

| Time after HAS or PBS transfer (min) | Fluorescence Units of PORPHYRIN Loaded 2:1 Soy-PC:DSPG Liposome Solution (4 ml): | | | | Fluorescence Units of PBS Solution (4 ml): | |
|---|---|---|---|---|---|---|
| | (b)(ii) Upon 0.2 ml PBS transfer | (b)(ii) Upon 0.4 ml PBS transfer | (b)(i) Upon 0.2 ml (=0.5 mg/ml) HSA transfer | (b)(i) Upon 0.4 ml (=1.0 mg/ml) HSA transfer | (b)(ii) Upon 0.2 ml (=0.5 mg/ml) HSA transfer | (b)(iii) Upon 0.4 ml (=1.0 mg/ml) HSA transfer |
| 0.0 | 612.47 | 622.20 | 644.27 | 583.63 | 0.27 | 0.62 |
| 0.5 | 522.00 | 481.92 | 476.70 | 351.73 | 1.24 | 1.36 |
| 1.0 | 519.26 | 477.43 | 426.07 | 304.44 | 1.38 | 1.48 |
| 2.0 | 509.90 | 490.11 | 409.92 | 290.36 | 1.00 | 1.49 |
| 3.0 | 497.42 | 477.23 | 378.56 | 279.99 | 1.05 | 1.41 |
| 4.0 | 490.58 | 460.40 | 366.67 | 270.59 | 1.29 | 1.56 |
| 5.0 | 487.49 | 449.67 | 360.69 | 270.76 | 1.16 | 1.33 |
| 6.0 | Not recorded | 449.10 | 359.94 | 269.48 | 1.00 | 1.41 |
| 7.0 | 452.20 | 444.98 | 359.64 | 262.74 | Not recorded | Not recorded |
| 8.0 | 447.77 | 431.41 | Not recorded | 261.03 | Not recorded | Not recorded |
| 9.0 | 434.51 | 428.54 | Not recorded | Not recorded | Not recorded | Not recorded |
| 10.0 | 420.38 | 415.06 | Not recorded | Not recorded | Not recorded | Not recorded |

TABLE 3

Fluorescence units upon interaction between 1:20 GALLIUM CHLORIDE
DEUTEROPORPHYRIN-IX DIMETHYL ESTER:Lipid
(3:1 Soy-PC:DSPG) liposome, Human Serum Albumin and PBS

| Time After HAS or PBS transfer (min) | Fluorescence Units of GALLIUM CHLORIDE DEUTEROPORPHYRIN-IX DIMETHYL ESTER Loaded 3:1 Soy-PC:DSPG Liposome Solution (4 ml): | | | | Fluorescence Units of PBS Solution (4 ml): | |
|---|---|---|---|---|---|---|
| | (b)(ii) Upon 0.2 ml PBS transfer | (b)(ii) Upon 0.4 ml PBS transfer | (b)(i) Upon 0.2 ml (=0.5 mg/ml) HAS transfer | (b)(i) Upon 0.4 ml (=1.0 mg/ml) HAS transfer | (b)(ii) Upon 0.2 ml (=0.5 mg/ml) HAS transfer | (b)(iii) Upon 0.4 ml (=1.0 mg/ml) HSA transfer |
| 0.0 | 634.31 | 618.13 | 654.93 | 594.60 | 0.81 | 0.99 |
| 0.5 | 526.60 | 507.46 | 448.25 | 352.18 | 0.92 | 1.71 |
| 1.0 | 529.31 | 508.95 | 411.88 | 310.32 | 1.11 | 1.94 |
| 2.0 | 515.82 | 526.48 | 388.63 | 299.50 | 0.94 | 1.56 |
| 3.0 | 483.18 | 521.49 | 382.64 | 294.55 | 1.08 | 1.78 |
| 4.0 | 487.93 | 506.71 | 369.47 | 294.60 | 0.76 | 1.66 |
| 5.0 | 531.85 | 514.49 | 356.74 | 296.06 | 1.05 | 1.51 |
| 6.0 | 521.17 | 506.25 | 367.70 | Not recorded | 0.90 | Not recorded |
| 7.0 | Not recorded | Not recorded | 371.58 | Not recorded | Not recorded | Not recorded |
| 8.0 | Not recorded | Not recorded | 373.04 | Not recorded | Not recorded | Not recorded |

In this example intrinsic porphyrin fluorescence was reduced from 644 to 476 units within 30 seconds of mixing with 0.2 ml (0.5 mg/ml) HSA and has stabilized after 3 minutes. Porphyrin fluorescence was reduced from 583 to 351 units within 30 seconds of mixing with 0.4 ml of HSA (1.0 mg/ml). The fluorescence reduction in the first instance was greater than the latter indicating that the drug had bound to the HSA, which may be the result of drug being released from the liposome or from fluorescence quenching due to drug mixing with tryptophan and tyrosine residues in the HSA, tryptophan and tyrosine both being intrinsically fluorescent.

It was also noted that the amount of drug fluorescence reduction was directly proportional to HSA concentration. Even though, fluorescence reduction appeared to be less compared to results with HDL and LDL, it should be noted that HSA concentration was only 1.0 mg/ml while HSA concentration in blood is closer to 30 mg/ml, thus GC-DPDE-HSA binding in the blood stream may be much greater than that indicated by these experiments.

The gradual fluorescence decrease when drug-loaded liposome was mixed with PBS in this case could be explained by the fact that the PBS merely diluted the liposome solution or the liposome could have interacted with the plastic cuvette over time. Further testing confirmed that the liposome bilayer remained intact with the drug contained therein on mixing with PBS.

The above experiment was conducted with both 2:1 and 3:1 soy PC:DSPG, the results indicating that drug binding efficiency with HSA is not affected by the charge stability of the liposome.

Example 3

Example 3 demonstrates the lability of liposomes of this invention in the presence of LDL and HDL with PBS again used as a control comparison. Soy PC:DSPG shell liposomes at ratio of 2:1 and 3:1 were again used and the GC-DPDE was again diluted until UV/VIS spectroscopy afforded a 0.1-0.2 AU reading. The average liposome size was 70.7-72.6 nm. The GC-DPDE-laden liposomes were then contacted with HDL (Sigma-Aldrich L1567-10MG, dissolved in PBS to a concentration of 5 mg/ml) or LDL (Sigma-Aldrich L8292-1VL, diluted with PBS to a concentration of 5 mg/ml) and with standard saline solution (PBS) by extracting 0.2/0.4 ml of drug-loaded liposome and replacing with 0.2/0.4 ml of either HDL, LDL or PBS and screening using a microplate reader to determine the amount of drug, if any, that was released from the heavily loaded liposome by the HSA or into the PBS The results are shown in Table 4 and 5.

TABLE 4

Fluorescence units upon interaction between 1:20 GALLIUM CHLORIDE DEUTEROPORPHYRIN-IX DIMETHYL ESTER:Lipid (2:1 Soy-PC:DSPG) liposome, HDL or LDL, and PBS

| Time after HDL or LDL transfer (min) | Fluorescence Units of PORPHYRIN Loaded 2:1 Soy-PC:DSPG Liposome solution (4 ml): | | | | | Fluorescence Units of PBS (4 ml) | | |
|---|---|---|---|---|---|---|---|---|
| | (c)(i) Upon 0.2 ml HDL transfer | | (c)(i) Upon 0.2 ml LDL transfer | | (c)(ii) Upon 0.2 ml PBS transfer | (c)(iii) Upon 0.2 ml LDL transfer | (c)(iii) Upon 0.2 ml HDL transfer |
| | 1st set | 2nd set | 1st set | 2nd set | | | |
| 0.0 | 538.07 | 572.68 | 533.82 | 517.79 | 543.51 | 0.78 | 0.51 |
| 0.5 | 155.02 | 168.22 | 167.55 | 157.52 | 490.02 | 5.58 | 6.41 |
| 1.0 | 152.57 | 168.47 | 155.03 | 143.01 | 487.81 | 4.27 | 6.06 |
| 2.0 | 153.44 | 168.34 | 151.33 | 142.48 | 457.82 | 4.14 | 6.41 |
| 3.0 | 154.12 | Not recorded | 151.02 | 140.74 | 448.00 | 4.27 | 6.44 |
| 4.0 | 157.25 | Not recorded | 152.78 | 138.85 | 444.03 | 4.37 | 6.46 |
| 5.0 | 159.41 | Not recorded | Not recorded | 144.24 | 448.98 | 4.02 | 6.29 |
| 6.0 | Not recorded | Not recorded | Not recorded | Not recorded | 439.88 | 4.16 | 6.38 |
| 7.0 | Not recorded | Not recorded | Not recorded | Not recorded | 439.92 | Not recorded | Not recorded |
| 8.0 | Not recorded | Not recorded | Not recorded | Not recorded | 427.80 | Not recorded | Not recorded |
| 9.0 | Not recorded | Not recorded | Not recorded | Not recorded | 412.96 | Not recorded | Not recorded |

TABLE 5

Fluorescence units upon interaction between 1:20 PORPHYRIN: Lipid (3:1 Soy-PC:DSPG) liposome, HDL or LDL, and PBS

| Time after HDL or LDL transfer (min) | Fluorescence Units of PORPHYRIN Loaded 3:1 Soy-PC:DSPG Liposome Solution (4 ml): | | | | | Fluorescence Units of PBS (4 ml) | | |
|---|---|---|---|---|---|---|---|---|
| | (c)(i) Upon 0.2 ml HDL transfer | | (c)(i) Upon 0.2 ml LDL transfer | | (c)(ii) Upon 0.2 ml PBS transfer | (c)(iii) Upon 0.2 ml LDL transfer | (c)(iii) Upon 0.2 ml HDL transfer |
| | 1st set | 2nd set | 1st set | 2nd set | | | |
| 0.0 | 673.76 | 534.77 | 683.17 | 558.62 | 644.07 | 0.94 | 1.05 |
| 0.5 | 172.30 | 145.52 | 209.42 | 184.28 | 553.33 | 5.14 | 6.81 |
| 1.0 | 172.50 | 144.26 | 193.31 | 169.42 | 547.68 | 5.08 | 6.51 |
| 2.0 | 171.51 | 144.05 | 188.65 | 165.13 | 548.71 | 5.21 | 6.52 |

TABLE 5-continued

Fluorescence units upon interaction between 1:20 PORPHYRIN: Lipid
(3:1 Soy-PC:DSPG) liposome, HDL or LDL, and PBS

| Time after HDL or LDL transfer (min) | Fluorescence Units of PORPHYRIN Loaded 3:1 Soy-PC:DSPG Liposome Solution (4 ml): | | | | (c)(ii) Upon 0.2 ml PBS transfer | Fluorescence Units of PBS (4 ml) | |
|---|---|---|---|---|---|---|---|
| | (c)(i) Upon 0.2 ml HDL transfer | | (c)(i) Upon 0.2 ml LDL transfer | | | (c)(iii) Upon 0.2 ml LDL transfer | (c)(iii) Upon 0.2 ml HDL transfer |
| | 1st set | 2nd set | 1st set | 2nd set | | | |
| 3.0 | 172.20 | 145.88 | 182.99 | 162.55 | 534.80 | 5.09 | 6.90 |
| 4.0 | 173.13 | 145.77 | 184.37 | 160.72 | 528.08 | 4.69 | 6.36 |
| 5.0 | 174.86 | 147.32 | 181.57 | 161.66 | 521.51 | 4.93 | 6.55 |
| 6.0 | 174.53 | 147.62 | 179.58 | 159.43 | 514.85 | 5.15 | 6.97 |

Regardless of 2:1 or 3:1 soy PC:DSPG ratio, a drastic reduction in fluorescence (form about 600 to about 167 units) was observed within 30 seconds when 0.2 ml of HDL or LDL were mixed with drug-loaded liposome. Clearly, the drug had rapidly and strongly bound to HDL and LDL almost immediately upon contact and the reduction in fluorescence reflected either drug being released from the liposome or fluorescence quenching due to drug mixing with tryptophan and tyrosine in the HDL and LDL.

Example 4

Native-PAGE was used to investigate GS-DPDE:liposome protein interaction. PC:DSPG was again used at 3:1 ratio with a drug:lipid ratio of 1:20, which afforded liposomes of average size 93.2 nm. HDL and HSA were prepared in the same manner as in Examples 2 and 3.

Figure 1:
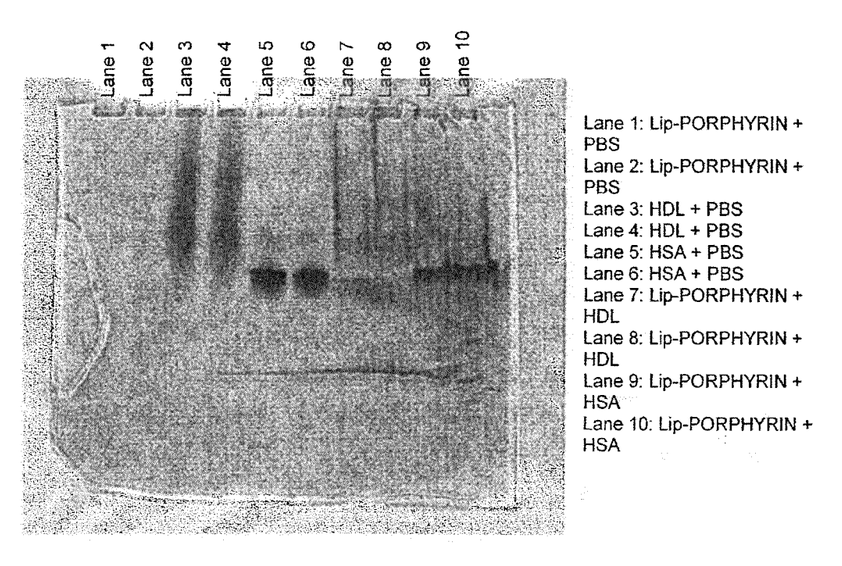
FIG. 1 is a native-:PAGE gel electrophoresis of various combinations of the components of the current invention: Lane 1: Lip-porphyrin+PBS; Lane 2: Lip-porphyrin+PBS; Lane 3: HDL+PBS; Lane 4: HDL+PBS; Lane 5: HSA+PBS; Lane 6: HSA+PBS; Lane 7: Lip-porphyrin+HDL; Lane 8: Lip-porphyrin+HDL; Lane 9: Lip-porphyrin+HSA; Lane 10: Lip-porphyrin+HSA.

The GC-DPDE-liposome formulation was mixed with protein (HDL or HAS) in a 1:1 weight ratio. Sampleloading buffer was added to the mix in a 1:5 ratio. 12 μl of liposome-protein mix (12 μg drug:12 μg protein) was loaded into each well of a 10-well Novex® Tris-glycine 4-12% polyacrylamide gel (Invitrogen). A native-PAGE was performed using the Invitrogen XCell-SureLock® Mini-Cell at 125 V for 1.5 hours. Liposome-PBS, HDL-PBS and HAS-PBS mix were used as controls. After electrophoresis, the gel was released from the plastic case and stained with a Coomassie solution (BioRad) for 30 minutes. The gel was then unstained in Coomassie destaining solution (BoiRad) for 2 hours. The gel was then washed three times with de-ionized water and transferred to 5% glycerol and left for 10 minutes. The gel was then sandwiched in between two cellophane films and dried overnight. The results are shown in FIG. 1.

Lanes 1-2, 3-4 and 5-6 are the liposome-porphyrin+PBS, HDL+PBS and HSA+PBS controls. Lanes 7-8 and 9-10 show the protein distribution after the HDL and HSA were mixed with the liposome-porphyrin formulation. When HDL alone was separated through the gel, a smear was obtained. When the liposome-porphyrin formulation was added to the HDL, however, the protein smear was not observed. When HSA was separated through the gel, a sharp protein band was observed with a faint protein band above it. When HSA was mixed with the liposome-porphyrin drug, the sharp protein band was reduced and the faint band was not longer in evidence. The missing smears and bands form the liposome-porphyrin and protein mix indicates that the drug may have bound to the protein, thus altering its isoelectric properties and retarding its mobility through the polyacrylamide matrix.

What is claimed:

1. A method of targeting drug delivery to a vascular lesion, comprising:
   providing a core-shell carrier comprising a lipophilic shell layer that is unstable to a plasma protein;
   providing a non-photodynamic hydrophobic drug linked to a porphyrin and loaded into the core-shell carrier, the porphyrin comprising a deuteroporphyrin IX diester; and
   administering the linked drug/porphyrin-loaded core-shell carrier into the bloodstream of a patient in need thereof;
   wherein,
      when the core-shell carrier contacts a plasma protein in the patient's bloodstream, the core-shell carrier is disrupted, releasing the linked drug/porphyrin, which then forms a complex with a plasma protein that may be the same as or different than the plasma protein that caused the disruption of the core-shell carrier;
      wherein the linked drug/porphyrin comprises a biocompatible, biodegradable linker joining the drug to the porphyrin; and
      wherein the core-shell carrier is selected from the group consisting of a plasma protein unstable micelle, a plasma protein unstable liposome and a plasma protein unstable polymerosome.

2. The method of claim 1, wherein the core-shell carrier is a plasma protein unstable micelle, or a plasma protein unstable polymerosome.

3. The method of claim 1, wherein the core-shell carrier comprises a plasma protein unstable liposome.

4. The method of claim 3, wherein the linked drug/porphyrin is loaded into a lipid bilayer of the plasma protein unstable liposome.

5. The method of claim 4, wherein the plasma protein unstable liposome comprises soy phosphatidylglycerol, hydrogenated soy phosphatidylglycerol, distearoyl phosphatidylglycerol, soy phosphatidylcholine, hydrogenated soy phosphatidylcholine or any combination thereof.

6. The method of claim 1, wherein the diester is a dimethyl ester.

7. The method of claim 1, wherein the vascular lesion comprises an atherosclerotic plaque, a restenotic lesion, a vulnerable plaque or a peripheral arterial lesion.

8. The method of claim 1, wherein the plasma protein that disrupts the core-shell carrier and the plasma protein that forms a complex with the linked drug/porphyrin independently comprise low density lipoprotein, high density lipoprotein, human serum albumin or any combination thereof.

9. The method of claim 1, wherein the non-photodynamic hydrophobic drug is selected from the group consisting of rapamycin, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin, zotarolimus, everolimus, biolimus, temsirolimus, deforolimus, novolimus, myolimus, and combinations thereof.

10. The method of claim 9, wherein the non-photodynamic hydrophobic drug is selected from the group consisting of everolimus and zotarolimus.

11. The method of claim 1, wherein the linked drug/porphyrin-laden plasma protein unstable core-shell carrier is administered systemically.

12. The method of claim 1, wherein the linked drug-porphyrin-laden plasma protein unstable core-shell carrier is administered locally.

13. The method of claim 12, wherein local administration comprises use of an implantable medical device.

14. The method of claim 13, wherein the implantable medical device is a stent.

15. The method of claim 5, wherein the non-photodynamic hydrophobic drug is selected from the group consisting of rapamycin, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin, zotarolimus, everolimus, biolimus, temsirolimus, deforolimus, novolimus, myolimus, and combinations thereof.

* * * * *